United States Patent
Carrie

[11] Patent Number: 5,591,132
[45] Date of Patent: Jan. 7, 1997

[54] EPIDURAL CATHETER

[76] Inventor: Len E. S. Carrie, 104 Cumnor Hill, Oxford OX2 9HY, England

[21] Appl. No.: 577,019
[22] Filed: Dec. 22, 1995

[30] Foreign Application Priority Data

Jan. 25, 1995 [GB] United Kingdom ............ 9501424

[51] Int. Cl.$^6$ .................................................. A61M 5/178
[52] U.S. Cl. ........................... 604/158; 604/164; 604/51
[58] Field of Search ................................... 604/280–282, 604/264, 158, 161, 164–165, 51, 53

[56] References Cited

U.S. PATENT DOCUMENTS

| | | |
|---|---|---|
| 4,518,383 | 5/1985 | Evans . |
| 4,694,838 | 9/1987 | Wijayarthna et al. . |
| 4,738,667 | 4/1988 | Galloway . |
| 4,747,840 | 5/1988 | Ladika et al. . |
| 4,973,305 | 11/1990 | Goltzer . |
| 5,163,928 | 11/1992 | Hobbs et al. . |
| 5,167,647 | 12/1992 | Wijkamp et al. . |
| 5,221,269 | 6/1993 | Miller et al. . |

FOREIGN PATENT DOCUMENTS 0497285  5/1992  European Pat. Off. .

*Primary Examiner*—Randall L. Green
*Assistant Examiner*—Perry E. Van Over
*Attorney, Agent, or Firm*—Pollock, Vande Sande & Priddy

[57] ABSTRACT

An epidural catheter with a patient end that forms a coil in its natural state, either in the plane of the length of the catheter or helically, so that, when inserted in the epidural space, the coil projects into the epidural space to ensure adequate retention but still ensuring that anaesthetic fluid emerges from side openings in the coil close to the point of insertion.

11 Claims, 2 Drawing Sheets

EPIDURAL CATHETER

BACKGROUND OF THE INVENTION

This invention relates to epidural catheters.

Epidural catheters are used to introduce anaesthetic fluid into the epidural space. The effectiveness of the anaesthesia block produced is dependent on the anaesthetic being administered in the correct location. Conventional epidural catheters are straight and flexible. They are usually closed at the tip and have several side openings through which fluid can emerge from the catheter. It has been found that, if the tip of the catheter is inserted more than about 10–20 mm into the epidural space, the tip seldom remains in the desired location near the site of insertion but passes into the lateral or anterior parts of the epidural space. It is thought that this may sometimes be the reason why epidural anaesthesia occasionally produces imperfect blocks. Some anaesthetists prefer to leave a shorter length of catheter projecting into the epidural space, to reduce the risk of the tip of the catheter moving away from the insertion site. However, if an insufficient length of catheter projects into the epidural space, movement between the skin and ligamentum flavum can pull the catheter out of the epidural space and result in injection of anaesthetic outside the epidural space.

BRIEF SUMMARY OF THE INVENTION

It is an object of the present invention to provide an improved epidural catheter.

According to one aspect of the present invention there is provided an epidural catheter having a patient end that forms into a coil in its natural state.

In this way, a sufficient length of catheter can be inserted into the epidural space to ensure that it is not pulled out by movement between the skin and ligamentum flavum and yet the holes through which the anaesthetic fluid emerges can be kept in the region of the insertion site.

The coil preferably lies in the plane of the catheter and is formed by a region about 50 mm long at the patient end of the catheter, giving the coil a diameter of about 10 mm. Alternatively, the coil may be helical. The patient end of the catheter is preferably closed and rounded, the catheter having at least one side opening close to its patient end. The catheter may have a plurality of openings spaced along a region about 4 mm long. The catheter preferably has a diameter of about 1 mm.

It has previously been proposed in EP-A-497285 to coil the tip of a fine 30G spinal catheter introduced into the subarachnoid space in order to ease insertion by reducing obstruction by the anterior wall of the subarachnoid space. Also, this reduces the risk of the tip of the catheter passing caudally and causing cauda equina syndrome. No one, however, has previously addressed the problem of epidural catheters in the same way. Epidural catheters differ from spinal catheters in that they are generally of larger diameter and are designed for insertion into the epidural space, in which their direction of passage is determined by surrounding tissues, especially fat and veins. By contrast, the subarachnoid space is filled with cerebrospinal fluid and nerve roots which, with the anterior wall of the space are the only significant factors influencing the direction taken by the spinal catheter. The considerations involved in the design of spinal and epidural catheters are, therefore, quite different.

Two epidural catheters in accordance with the present invention, will now be described, by way of example, with reference to the accompanying drawings.

DETAILED DESCRIPTION OF THE PREFERRED EMBODIMENTS

Figure 1:
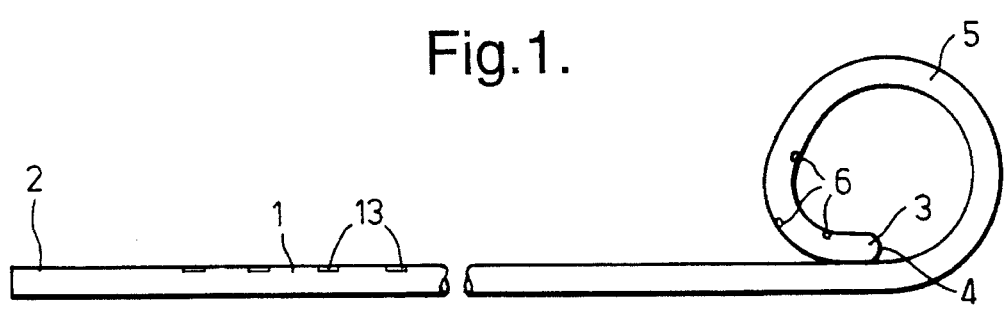
FIG. 1 is a side elevation view of a first catheter.

With reference to FIG. 1, the epidural catheter comprises a tube 1 of a flexible plastics material, such as nylon. The tube is about 915 mm long and is circular in section, with an external diameter of 1 mm and an internal diameter of 0.58 mm. Along the major part of its length, the tube is substantially straight. The machine end 2 of the catheter is square, plain and open, enabling it to be joined to any conventional epidural connector.

The patient end 3 of the catheter has a smoothly rounded, closed tip 4 and, in its natural state, forms a coil 5 in the plane of the straight part of the catheter. The coil 5 is about 10 mm in external diameter and is formed from a single turn of the catheter along a region about 50 mm long. The catheter has three openings 6 spaced from one another along a region 4 mm long extending from the patient end 3 of the coil 5. The openings 6 are distributed around the circumference of the catheter.

Figure 2:
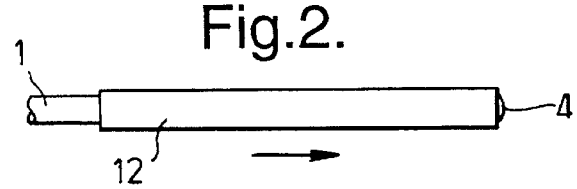
FIG. 2 is an enlarged side elevation view of the patient end of the catheter just prior to insertion.
Figure 3A:
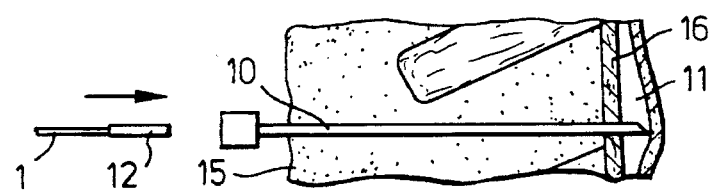
FIGS. 3A to 3C illustrate schematically three steps in the insertion of the catheter.
Figure 3B:
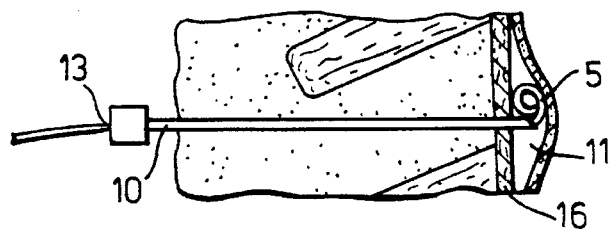

In use, a conventional, hollow epidural needle 10 is inserted into the epidural space 11 in the usual way, as shown in FIG. 3A. The needle 10 is preferably one that has a straight shaft of Tuohy design so that the catheter emerges axially of the needle. When the needle 10 is correctly located, a plastic sleeve 12 is slid along the catheter 1 from its machine end 2 until it reaches the coiled region at the patient end 3. The coil 5 is straightened, as shown in FIG. 2, by sliding the sleeve 12 forwardly until the tip of the catheter is flush with the patient end of the sleeve. The projecting patient end of the catheter 1 is now substantially straight, enabling it to be inserted into the rear end of the needle 10. The diameter of the sleeve 12 is such that it cannot enter the needle. The catheter 1 is pushed into the needle 10 by a measured distance, as indicated by markings 13 on the catheter, so that the catheter emerges from the tip of the needle by a distance of about 40–50 mm. As the catheter emerges from the needle 10, it resumes its natural, coiled state, as shown in FIG. 3B. The needle 10 is then withdrawn, leaving the catheter in position.

Figure 3C:
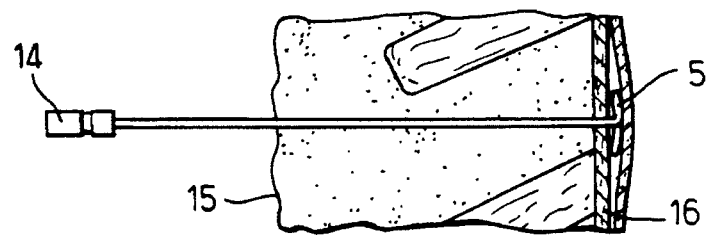

After removal of the needle 10, the anterior wall of the epidural space can relax, flattening the coil 5 against the ligamentum flavum 16. The machine end 2 of the catheter 1 is connected to a conventional epidural catheter connector 14, in the usual way, as shown in FIG. 3C so that anaesthetic fluid can be supplied to the catheter, such as via a syringe. The length of the catheter left projecting into the epidural space 11 is between 40–50 mm, which is sufficient to ensure that any movement between the skin 15 and the ligamentum flavum 16 will not pull the catheter out of the epidural space 11. The length of catheter left projecting into the epidural space is also chosen such that only the coiled part 5 of the catheter remains in the epidural space The coiled configuration of the catheter ensures that anaesthetic fluid always emerges into the epidural space 11 close to the insertion site, where it is most effective.

Figure 4:
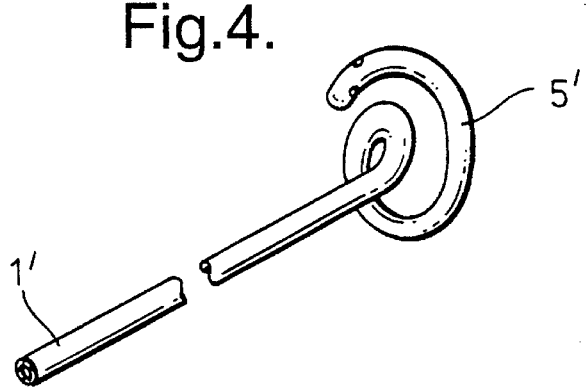
FIG. 4 is a perspective view of an alternative catheter.
Figure 5A:
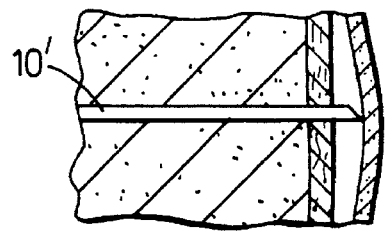
FIGS. 5A to 5C illustrate schematically three steps in the insertion of the alternative to catheter.
Figure 5B:
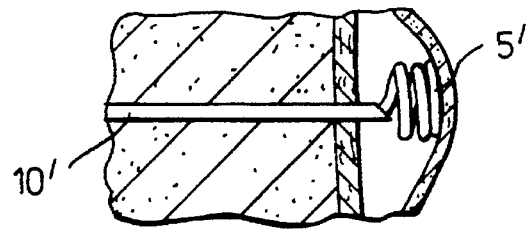
Figure 5C:
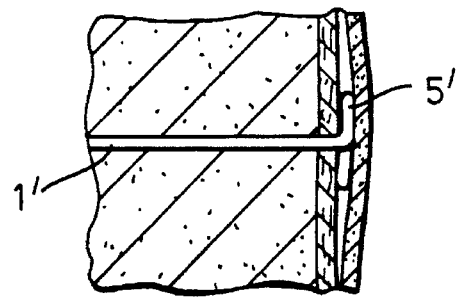

In the arrangement described above, the natural state of the coil is in the same plane as the major part of the length of the catheter. The coil could, however, be formed in a different plane, as shown in FIGS. 4 and 5. In this arrangement, the natural shape of the coil 5' is shown in FIG. 4 to be a tapering helix formed by the catheter taking a spiral path that increases progressively in radius towards the patient end of the catheter, with the axis along the center of the helix being aligned with the rear part of the catheter. After removal of the needle 10', the anterior wall of the epidural space bears on the patient end of the catheter and compresses it against the ligamentum flavum 16 so that the coil 5' is flattened in a plane at right angles to the major part of the length of the catheter, as shown in FIG. 5C. This configuration may be more likely to lie flat in the epidural space under the flattening action of the epidural tissues. The previously-described configuration may be more likely to twist and hold the epidural space open.

What I claim is:

1. An epidural catheter comprising a tube with a patient end that forms into a coil in its natural state.

2. A catheter according to claim 1, wherein said coil lies in a plane including the length of the catheter.

3. A catheter according to claim 1, wherein said coil is formed by a region about 50 mm long at said patient end of the catheter.

4. A catheter according to claim 1, wherein said catheter has a diameter of about 10 mm.

5. A catheter according to claim 1, wherein said coil is helical.

6. A catheter according to claim 1, wherein said patient end of the catheter is closed and rounded, and wherein said catheter has at least one side opening close to said patient end.

7. A catheter according to claim 6, wherein said catheter has a plurality of openings close to its patient end, and wherein said openings are spaced along a region about 4 mm long.

8. A catheter according to any claim 1, wherein said catheter has an external diameter of about 1 mm.

9. An epidural catheter comprising an elongated tube with a patient end, wherein said patient end is closed and rounded, wherein said patient end forms into a coil in a plane including the length of the catheter in its natural state, and wherein the catheter has a plurality of side openings at said patient end along said coil.

10. An epidural catheter comprising a tube with a patient end, wherein said patient end is closed and rounded, wherein said patient end forms into a helical coil in its natural state, and wherein the catheter has a plurality of side openings at said patient end along said coil.

11. A method of performing epidural anaesthesia comprising the steps of:

introducing a hollow needle having a tip so that said tip is located in the epidural space, providing a catheter of a kind having a patient end that forms into a coil in its natural state, straightening said patient end and inserting it into the needle until the patient end of the catheter emerges from the patient end of the needle and forms a coil within the epidural space, removing said needle, and introducing anesthetic fluid into the epidural space via the catheter.

\* \* \* \* \*